Figure 1A:
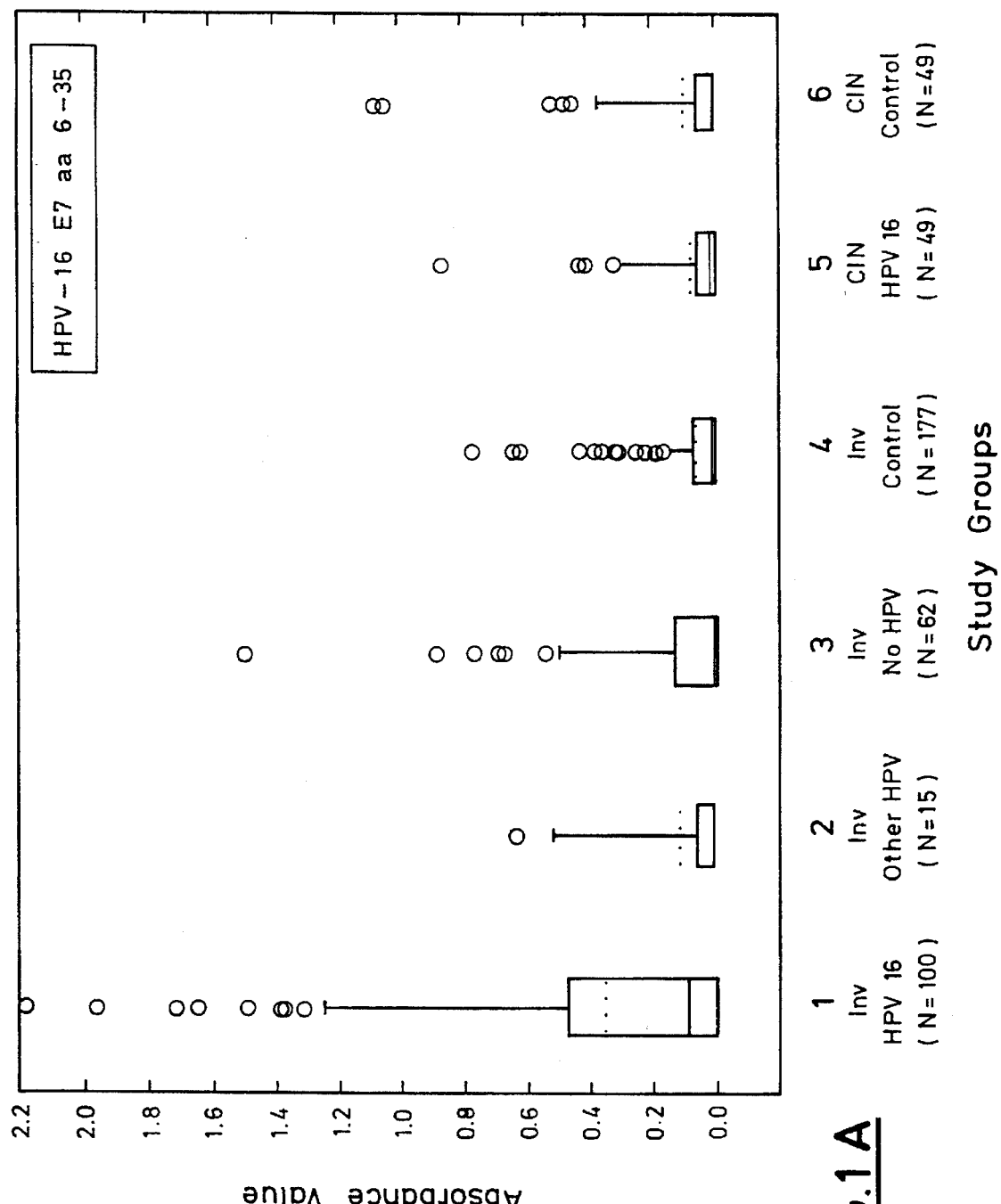

United States Patent [19]

Müller et al.

[11] Patent Number: 5,629,161
[45] Date of Patent: May 13, 1997

[54] USE OF HVP-16 E6 AND E7-GENE DERIVED PEPTIDES TO DIAGNOSE HPV-16-ASSOCIATED INVASIVE CERVICAL CANCER

[75] Inventors: Martin Müller, Heidelberg; Lutz Gissmann, Wiesloch, both of Germany

[73] Assignee: Behringwerke Aktiengesellschaft, Marburg, Germany

[21] Appl. No.: 363,586

[22] Filed: Dec. 23, 1994

Related U.S. Application Data

[63] Continuation of Ser. No. 109,469, Aug. 20, 1993, abandoned, which is a continuation of Ser. No. 909,296, Jul. 9, 1992, abandoned.

[30] Foreign Application Priority Data

Jul. 13, 1991 [EP] European Pat. Off. ............ 91111720

[51] Int. Cl.$^6$ .................... G01N 33/53; C07K 16/44; C07K 16/08
[52] U.S. Cl. .................... 435/7.1; 530/324; 530/325; 530/326; 530/327; 530/388.3; 530/387.9; 530/389.1; 530/389.4
[58] Field of Search .................... 435/5, 7.1, 7.9; 530/324–327, 388.3, 387.9, 389.1, 389.4

[56] References Cited

U.S. PATENT DOCUMENTS 5,180,806  1/1993  Dillner et al. ............ 530/326

FOREIGN PATENT DOCUMENTS

| | | |
|---|---|---|
| 0257754A2 | 3/1988 | European Pat. Off. . |
| 0344940A2 | 12/1989 | European Pat. Off. . |
| 0375555A1 | 6/1990 | European Pat. Off. . |
| 0386734A2 | 9/1990 | European Pat. Off. . |
| 0451550A2 | 10/1991 | European Pat. Off. . |
| 0451550A2 | 10/1992 | European Pat. Off. . |
| 90/10867 | 9/1990 | WIPO . |
| WO91/18294 | 11/1991 | WIPO . |
| WO92/05248 | 4/1992 | WIPO . |

OTHER PUBLICATIONS

Jochmus–Hudielka et al., 1989, J. National Cancer Institute, 81(22):1698.
Seedorf et al., Embo J., 1987, 6(1):132.
Harris et al., Tibtech, 1993, 11:42, Therapeutic . . . Age Hird et al., Cancer & Genes, 1990, pp. 183–189.
Osbend et al., Immunol. today, 1990, 11:193, Problems . . . immunotherapy.
Waldmann et al, Monoclonal . . . Therapy, 1991, Science 252:1657–62.
Thorpe et al, Antibody . . . A Review, 1985, In. Monoclonel Antibodies '84:Biological & Clinical Applications.
Journal of General Virology, 71, No. 11, Nov. 1990, pp. 2709–2717, M. Mueller et al: "Identification of seroreactive regions . . . E7 and L1."
Journal of Virology, vol. 65, No. 3, Mar. 1991, pp. 1208–1218, S.A. Jenison et al.: "Characterization of . . . Types 16 and 18."
Microbial Pathogenesis, vol. 8, Mar. 1990, pp. 163–168, S. Olsnes et al.: "Protein toxins with intracellular targets."
Journal of Virology, vol. 64, No. 12, Dec. 1990, pp. 6121–6129, J. Rawls et al.: "Chemical Synthesis . . . for trans Activation."
Proc. Natl. Acad. Sci., USA, vol. 80, pp. 3812–3815, Jun. 1983.
Virology 145, 181–185 (1985).
Journal of the National Cancer Institute, 81 (22):, 1698–1704 (1989).
Journal of General Virology, 71: pp. 2709–2717 (1990).

*Primary Examiner*—Frank C. Eisenschenk
*Attorney, Agent, or Firm*—Finnegan, Henderson, Farabow, Garrett & Dunner, L.L.P.

[57] ABSTRACT

The present invention relates to the use of human pailloma-virus 16 (HPV-16) E7-gene derived peptides for the diagnostic identification of HPV-16-associated invasive cervical cancer.

8 Claims, 3 Drawing Sheets

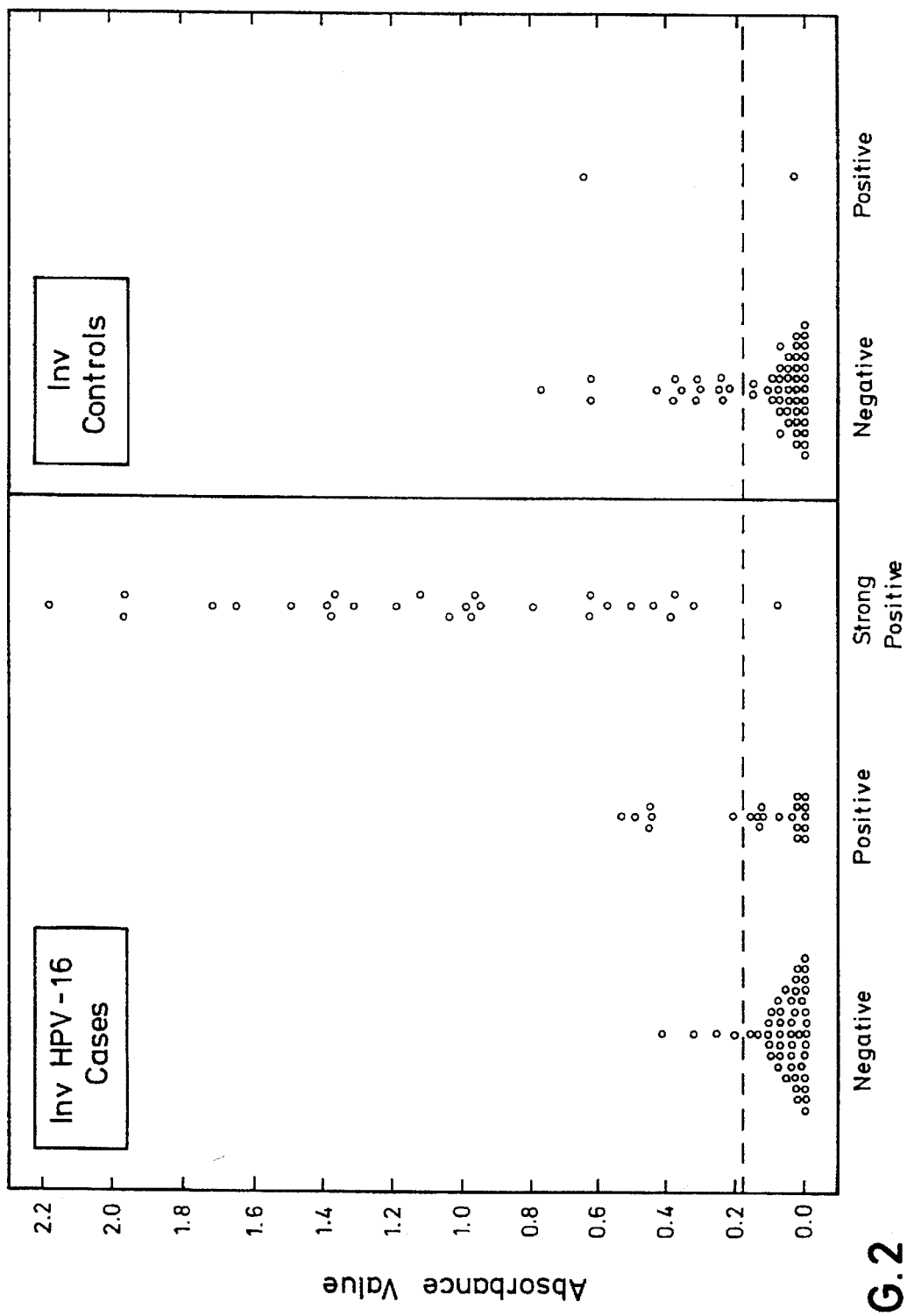
FIG. 2  In vitro transcription and translation radioimmunoprecipitation assay

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 30 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:1:

```
Pro Thr Leu His Glu Tyr Met Leu Asp Leu Gln Pro Glu Thr Thr Asp
1               5                   10                  15
Leu Tyr Cys Tyr Glu Gln Leu Asn Asp Ser Ser Glu Glu Glu
                20              25                  30
```

( 2 ) INFORMATION FOR SEQ ID NO:2:

( i ) SEQUENCE CHARACTERISTICS:
      ( A ) LENGTH: 25 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:2:

```
Asn Asp Ser Ser Glu Glu Glu Asp Glu Ile Asp Gly Pro Ala Gly Gln
1               5                   10                  15
Ala Glu Pro Asp Arg Ala His Tyr Asn
                20              25
```

( 2 ) INFORMATION FOR SEQ ID NO:3:

( i ) SEQUENCE CHARACTERISTICS:
      ( A ) LENGTH: 23 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:3:

```
Met His Gln Lys Arg Thr Ala Met Phe Gln Asp Pro Gln Glu Arg Pro
1               5                   10                  15
Arg Lys Leu Pro Gln Leu Cys
                20
```

( 2 ) INFORMATION FOR SEQ ID NO:4:

( i ) SEQUENCE CHARACTERISTICS:
      ( A ) LENGTH: 30 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:4:

```
Met Phe Gln Asp Pro Gln Glu Arg Pro Arg Lys Leu Pro Gln Leu Cys
1               5                   10                  15
Thr Glu Leu Gln Thr Thr Ile His Asp Ile Ile Leu Glu Cys
                20              25                  30
```

USE OF HVP-16 E6 AND E7-GENE DERIVED PEPTIDES TO DIAGNOSE HPV-16-ASSOCIATED INVASIVE CERVICAL CANCER

This application is a continuation of application Ser. No. 08/109,469, filed Aug. 20, 1993, now abandoned; which is a continuation of Ser. No. 07/909,296, filed Jul. 9, 1992, now abandoned.

This invention relates to the use of human papillomavirus 16 (HPV-16) E6 and E7-gene derived peptides for the diagnostic identification of HPV-16-associated invasive cervical cancer.

Furthermore, this invention relates to antibodies with affinity for a specific HPV-16 E6 or E-7-gene derived peptides which may be agents for the production of a medicament for the treatment of HPV-16 invasive cancer.

HPV-16 is a type of the human papillomavirus which has been first described in Proc. Natl. Acad. Sci., U.S.A., 80, 3813–3815 (1983). The DNA-sequence and the genome organization of HPV-16 have been published in Virology 145, 181–185 (1985).

HPV genomic sequences are recovered from a large majority of pre-invasive and invasive cervical cancers, and HPV-16 has been recognized to be the predominant HPV type in these tumors in studies all over the world (1). HPV-16 genome is present in about 50% of cervical cancers and is often integrated into the cellular DNA (2). Many attempts have been made to identify serologic markers of HPV-associated cancers. Previously, it was reported that serum antibodies to HPV-16 E-7-fusion protein were detected in 20.5% of invasive cervical cancer cases but in only 1.4–3.8% of control subjects (J. Natl. Cancer Inst. 81, page 1698, (1989)). EP-A-90 105 222.5 discloses specific seroreactive regions on HPV-16 proteins E4, E6, E7 and L1 and diagnostical kits for the identification of specific antibodies against HPV-16 E4, E6, E7 and L1 proteins. However, the interpretation of serologic data in all above-mentioned studies was difficult because the serum donors were not fully characterized virologically or epidemiologically.

The object of the present invention therefore was the identification of viral structures for the use as reliable diagnostic markers for HPV-16-associated invasive cervical cancer. Furthermore, the object of the present invention was to provide specific tools for the therapeutical control of HPV-16-associated invasive cancer.

The solution of these objects is the use of HPV-16 gene derived peptides for the diagnostic identification of HPV-16-associated invasive cervical cancer. The preferred peptides are HPV-16 E7 aa6–35, (SEQ ID NO: 1) HPV-16 E7 aa29–52, (SEQ ID NO: 2) HPV-16 E6 aa1–23 (SEQ ID NO: 3) and HPV-16 E6 aa8–37 (SEQ ID NO: 4) spanning the epitopes disclosed in J. Gen. Virol. 71, page 2709 (1990) (Table 3).

Furthermore, it was found that monoclonal or polyclonal antibodies having affinity to HPV-16 E6 or E7-gene derived peptides can be used as agents for the production of a medicament for the treatment of cervical cancer. A preferred aspect of the invention are antibodies with the above affinities which are bound to cytotoxic compounds (e.g. cholera toxin) which can be used to control tumor growth.

Sera from participants of a case-control study of cervical cancer were tested for reactivity with HPV-16 E6 and E7 peptides, and with in vitro translated full-length HPV-16 E6 or E7 polypeptide.

It was surprisingly found that serum reactivity to epitopes on E6 and E7 polypeptides is a marker of HP-16 associated invasive cervical cancer but not of HPV-16 associated pre-invasive disease or of invasive cervical cancer not associated with HPV-16.

In the ELISA studies, the clearest differences between cases and controls were found for reactivity to peptide E7 aa6–35 (37% vs. 9%), peptide E7 aa6–35 or E7 aa29–52 (49% vs. 17%), and peptide E7 aa6–35 and E7 aa29–52 (16% vs. 0%). Invasive cases in which HPV-16 was not recovered and cervical intraepithelial neoplasia (CIN) cases which probably harbored HPV-16 for months or years resembled the controls in their reactivity to the E6 and E7 peptides.

The cases of HPV-16-associated invasive cancer could be subdivided into those in whom HPV-16 was identified by Southern hybridization (Group 1A, n=39) and those in whom HPV-16 was identified by PCR, but not by Southern hybridization (Group 1B, n=67). The antibody prevalences to E6 and E7 peptides were higher in group 1A than in group 1B (49% vs. 30% for E7 aa6–38; 28% vs. 16% for E7 aa29–52; 64% vs. 39% for any E6 or E7 peptide; and 70% vs. 51% for any peptide). This suggested that in HPV-16-associated invasive cancer, a higher antibody prevalence was associated with higher amounts of HPV-16 in the gential tract specimen, which in turn, may reflect a larger tumor burden.

Immunologic intervention offers great promise for the control of tumors of viral etiology. E6 and E7 antigens are useful targets for diagnosis and imaging of HPV-associated cancers. Anti-E6/E7 antibodies tagged with cytotoxic molecules, such as cholera toxin, have therapeutic potential. Vaccination against early proteins of transforming viruses has been shown to prevent tumor development and in some cases to induce regression of tumors. E7 and E6 proteins are antigenic in the context of natural infection. This implies that cells expressing these proteins are to be accessible to immune effector mechanisms. This lends support to the rationale for pursuing immunologic approaches for diagnosis prevention and control of HPV-associated cancers.

EXAMPLES

Example 1

Four synthetic peptides were prepared representing two epitopes on E6 (E6 aa1–23 (SEQ ID NO: 3) and E6 aa8–37) (SEQ ID NO: 4) and two on E7 (E7 aa6–35 (SEQ ID NO: 1) and E7 aa29–52 (SEQ ID NO: 2) for use in ELISA with human sera. These peptides spanned epitopes on E6 and E7 (Table 3). The serum donors were subjects in a study of cervical cancer in Spain and Colombia in which incident cases of invasive cervical carcinoma and of cervical intraepithelial noeplasia grades 1–3 (CIN 1–3) were compared for behavioral and virological characteristics with their respective controls. The controls were population-based for invasive cancer cases and individually matched for CIN 1–3 cases. The disease status was confirmed by a panel of pathologists. Exfoliated cervical cells were tested for HPV by ViraPap$^R$, for the invasive component of the study and by ViraPap$^R$ and Southern hybridization for the CIN cases and controls. The cases were grouped on the basis of disease status and virologic diagnoses as follows:

group 1, invasive cases with HPV-16 (Inv-HPV-16);
group 2, invasive cases with other HPVs (Inv-other HPVs);
group 3, invasive cases where no HPVs were identified (Inv-no HPVs); and
group 5, CIN cases with HPV-16 (CIN-HPV-16).

Control group 4 for invasive cases (Inv-Control) and control group 6 for CIN cases (CIN-control) were selected from the corresponding controls of the Colombia-Spain study. Group 4 controls matched the age distribution and country of residence of Groups 1, 2 and 3 and group 6 controls were the individually matched controls of CIN cases in group 5. The invasive cases and controls (mean age, 50 years) were older than the CIN cases and controls (mean age, 33 years).

Serum specimens were tested in duplicate at a 1:25 dilution in ELISA with the E6 and E7 synthetic peptides. Wells of microtiter plates (Immunol II, Dynatech Laboratories, Arlington, Va.) were coated with 10 μg/ml of E7 aa6–38 or of 20 μg/ml of E7 aa29–52 in phosphate buffered saline, pH 7.2 or with 25 μg/ml of E6 aa1–23 or 10 μg/ml of E6 aa8–37 in 0.06M carbonate buffer, pH 9.6. The assay was completed with an anti-human IgG conjugated to horseradish peroxidase and ABTS substrate solution.

Figure 1B:
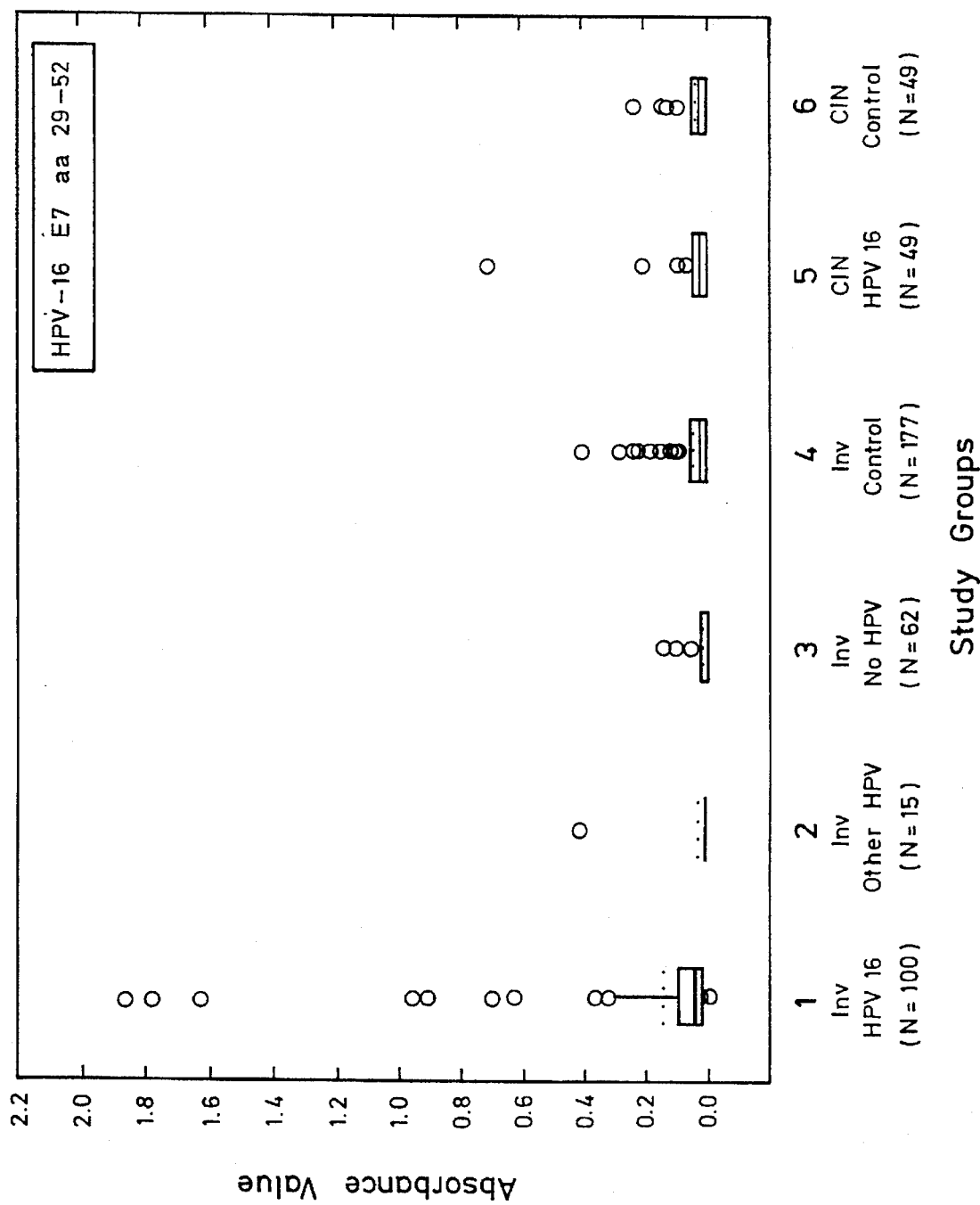

For each serum, the mean reactivity of buffer wells was subtracted from the mean reactivity of wells coated with peptide to calculate a net absorbance value. The distributions of absorbance values of cases (groups 1, 2, 3 and 5) were compared with those of their respective controls (groups 4 and 6) by Mann Whitney test. Significant differences in absorbance values were found for three of the four E6 and E7 peptides in the comparisons of group 1 cases with group 4 controls. The difference was most marked for peptide E7 aa6–35 (FIG. 1). The median absorbance value of peptide E7 aa6–35 with group 1 sera was 0.089 (0.482), as compared to the corresponding value of 0.009 (0.069) for group 4 sera; this difference was very highly significant ($p<0.00001$). Eighteen of the 100 sera in group 1 had absorbance values to peptide E7 aa6–35 which were higher than the highest absorbance value of 0.769 in the 177 sera of group 4. The distribution of absorbance values to peptide E7 aa6–35 in group 1 was also significantly different from that in group 2 ($p<0.05$), group 3 ($p<0.05$), group 5 ($p<0.001$), and group 6 ($p<0.0003$). Less pronounced but highly significant differences between group 1 and group 4 sera were also seen for reactivity to peptide E7 aa29–52 ($p<0.00001$) (FIG. 1), and to peptide E6 aa8–37 ($p<0.001$) (data not shown). The distribution of absorbance values to peptide E6 aa1–23 in group 1 sera was not significantly different from that in group 4 sera ($p=0.137$). As judged by the interquartile ranges (size of the boxes) in FIG. 1, there was a marked variability in the absorbance values of group 1 sera with peptide E7 aa6–35 but not with peptide E7 aa29–52. Cases of group 2 (Inv-other HPVs), 3 (Inv-no HPVs) and 5 (CIN-16) had reactivities to E6 and E7 peptides which were not significantly different from those of the corresponding controls. The differences in the reactivities of the two control groups 4 and 6 were also not statistically significant. These data indicated that the high reactivity to HPV-16 E6–E7 peptides was associated with HPV-16-associated invasive carcinoma but not with HPV-16-associated pre-invasive disease or with invasive disease not shown to be associated with HPV-16.

EXAMPLE 2

Individual sera were scored as antibody-positive or antibody-negative for each peptide, using a cut-off absorbance value which was based on the distribution of absorbance values of the control sera, excluding the outliers. The means and standard deviations of absorbance values of control sera were calculated (separately for groups 4 and 6) and sera with values greater than a mean +3 SD were excluded. The means and standard deviations were then recalculated and additional sera excluded, if necessary, by the same criteria. This process was repeated until none of the remaining sera were excluded, and the final mean +three standard deviations was taken as the cut-off value. The percentages of sera in the six groups with antibodies to individual peptides and to selected combinations of peptide, are shown in Table 1. In case-control comparisons, significant differences were found in antibody prevalences to each of the four E6 and E7 peptides, and for several combinations of E6–E7 peptides. These differences were noted only in comparisons of group 1 with group 4 (Table 1). 49% of group 1 sera and 17% of control sera had antibodies to at least one E6–E7 peptide ($p<0.00001$). The percent of sera in group 1 with antibodies to individual peptides ranged from a high of 37% for peptide E7 aa6–35 to a low of 10% for peptide E6 aa8–37; the corresponding percentages in group 4 were 9% and 1% (p values of $<0.00001$, for both comparisons). Case groups 3 and 5 did not differ from their corresponding controls in the antibody prevalences to the E6–E7 peptides, but differed from group 1 in the same way as the control group 4. Antibody to more than one peptide was common in group 1 but very uncommon in all other groups. Antibodies to both peptides of E7, both peptides of E6 and to all four E6–E7 peptides were found in 16%, 5% and 2%, respectively, in group 1 sera but not in a single serum from any of the other case or control groups ($p<0.00001$ for all three case-control comparisons).

EXAMPLE 3

In order to obtain independent confirmation of the seroreactivity with E7 peptides in ELISA, all available sera of group 1 (n=98) and 60 sera from group 4 (including 24 of 26 specimens in that group reactive with peptides E7 aa6–35 or E7 aa29–52) were tested in a radioimmunoprecipitation assay (RIPA) with labeled full-length E7 polypeptide, synthesized in an in vitro transcription and translation system (TT-RIPA). There was a marked difference in the reactivities of group 1 and group 4 sofa; 50% of group 1 sera, as compared to only 3% of group 4 sera, immunoprecipitated E7 polypeptide ($p<0.00001$). The correlation between full-length, E7 TT-RIPA and E7 peptide ELISA results was high for group 1 and low for group 4 sera (Table 2). All of the 15 group 1 sera which-were reactive with both E7 peptides were confirmed by TT-RIPA. A corresponding value for group 4 was not obtained because none of the sera in group 4 were reactive with both E7 peptides. For sera reactive in ELISA with peptide E7 aa6–35 alone, TT-RIPA confirmed 81% of group 1, but only 7% of group 4 sera ($p<0.00001$), and for sera negative with both peptides in ELISA, TT-RIPA was positive in 30% of group 1 and 0% of group 4 sera ($p<0.001$). For the few sera that were reactive with peptide E7 aa29–52 alone, TT-RIPA confirmed 20% of group 1 sera and 11% of group 4 sera. This difference was not significant ($p=0.6$). Eight of 27 E6 or E7 peptide-reactive sera from groups 2, 3, 5 and 6 gave positive results in TT-RIPA (data not shown).

EXAMPLE 4

The TT-RIPA results were categorized as negative positive and strong positive on the basis of the presence and the strength of the signal. The distributions of absorbance values with peptide E7 aa6–35 ELISA corresponding to these TT-RIPA results are shown in FIG. 2 for group 1 and group 4 sera. In group 1 sera, higher absorbance values in ELISA correlated very well with stronger signals in TT-RIPA; the mean absorbance values for RIPA scores of negative, positive and strong positives were 0.056, 0.159, and 1.05, respectively. In contrast, in group 4 only two sera were positive by TT-RIPA and none were strong positive. The mean absorbance value of TT-RIPA-negative sera in group 4 was 0.1145 as compared to the value of 0.056 in group 1. In tests of ELISA-positive sera with comparable absorbance values (between 0.18 and 0.8), TT-RIPA was positive far more often in group 1 (15 of 19 sera) than in group 4 (1 of 15 sera) (FIG. 2).

The above data from ELISA with E6 and E7 peptides clearly demonstrate that antibodies to epitopes on HPV-16 E6 and E7 are markers for HPV-16-associated invasive cancer.

TABLE 1

Antibodies to HPV-16 E6 and E7 peptides in sera of cervical neoplasia cases and controls

| | Percent of sera reactive[1] | | | | | |
|---|---|---|---|---|---|---|
| Peptide(s) | Group 1 (40 yrs)[2] n = 100 | Group 2 (55 yrs) n = 15 | Group 3 (55 yrs) n = 62 | Group 4 (50 yrs) n = 117 | Group 5 (33 yrs) n = 49 | Group 6 (33 yrs) n = 49 |
| Any E6-E7 | 49**** | 27 | 24 | 17 | 22 | 22 |
| E7 aa6-38 | 37**** | 20 | 21 | 9 | 16 | 14 |
| E7 aa29-52 | 21**** | 7 | 2 | 6 | 2 | 6 |
| E6 aa1-23 | 11** | 0 | 2 | 3 | 2 | 6 |
| E6 aa8-37 | 10**** | 0 | 0 | 1 | 2 | 0 |
| E7 aa6-38 or aa29-52 | 42**** | 27 | 23 | 15 | 18 | 20 |
| E7 aa6-38 and aa29-52 | 16 | 0 | 0 | 0 | 0 | 0 |
| E6 aa1-23 or aa8-37 | 16**** | 0 | 2 | 4 | 4 | 6 |
| E6 aa1-23 and aa8-37 | 5 | 0 | 0 | 0 | 0 | 0 |
| All four E6 and E7 | 2 | 0 | 0 | 0 | 0 | 0 |

[1]The cut-off values for peptides E7 aa6-35 (SEQ ID NO: 1), E7 aa29-52 (SEQ ID NO: 2), E6 aa1-23 (SEQ ID NO: 3) and E6 aa8-37 (SEQ ID NO: 4) were 0.18, 0.12, 0.36 and 0.51, respectively, on the basis of the distributions in group 4, and 0.11, 0.12, 0,55 and 0.62, respectively, on the basis of the distributions in group 4.
[2]Mean age
Case-control comparisons were made by Chi square test, using Fisher's exact probability where necessary.
denotes p < 0.01 and **denotes p < 0.0001.

TABLE 2

Correlation between results of ELISA and TT-RIPA in cases and controls

| ELISA | | TT-RIPA | | | |
|---|---|---|---|---|---|
| | | Group 1 | | Group 4 | |
| E7-01 peptide | E7-02 peptide | Number tested | Percent positive | Number tested | Percent positive |
| + | + | 15 | 100 | | |
| + | − | 21 | 81**** | 15 | 7 |
| − | + | 5 | 20 | 9 | 11 |
| − | − | 57 | 30**** | 36 | 0 |

****denotes p < 0.001 in comparisons of cases and controls. Description of TT-RIPA

TABLE 3

Peptides derived from the E6 and E7-gene of HPV 16

| Designation | Amino Acid Sequence |
|---|---|
| E7 aa6-35 | PTLHEYMLDLQPETTDLYCYEQLNDSSEEE (SEQ ID NO: 1) |
| E7 aa29-52 | NDSSEEEDEIDGPAGQAEPDRAHYN (SEQ ID NO: 2) |
| E6 aa1-23 | MHQKRTAMFQDPQERPRKLPQLC (SEQ ID NO: 3) |
| E6 aa8-37 | MFQDPQERPRKLPQLCTELQTTIHDIILEC (SEQ ID NO: 4) |

SHORT DESCRIPTION OF THE LEGENDS

FIG. 1:

Distribution of absorbance values of sera to peptides E7 aa 6-35 (SEQ ID NO: 1) and E7 aa29-52 (SEQ ID NO: 2). The summary statistics of each distribution are displayed in the box plot. The length of the box corresponds to the interquartile range, with the upper boundary of the box representing the 75th, and the lower boundary the 25th percentiles. The horizontal solid line in the box represents the median-value. The 90th percentile is shown by the small bar at the end of the line extending upward from the box plot. Each outlier absorbance value is shown individually by an open circle. In addition to the median value in the box plot, the mean absorbance value is shown with a broken line which may lie inside or outside the box. Distributions of cases and corresponding controls were compared by Mann Whitney test.

FIG. 2:

Comparison of TT-RIPA and peptide E7 aa6-35 (SEQ ID NO: 1) ELISA results in cancer cases with HPV-16 and controls. The horizontal dashed line represents the cut-off for seropositivity in the ELISA.

SEQUENCE LISTING

Seq. No. 1:
E7 aa6-35
PTLHEYMLDLQPETTDLYCYEQLNDSSEEE
human papillomavirus type 16
amino acid sequence Seq. No. 2:
E7 aa29-52
NDSSEEEDEIDGPAGQAEPDRAHYN
human papillomavirus type 16
amino acid sequence Seq. No. 3:
E6 aa1-23
MHQKRTAMFQDPQERPRKLPQLC
human papillomavirus type 16
amino acid sequence Seq. No. 4:
E5 aa8-37
MFQDPQERPRKLPQLCTELQTTIHDIILEC
human papillomavirus type 16
amino acid sequence

I claim:

1. A method of screening for HPV-16 associated invasive cervical carcinoma comprising the steps of:
   a) contacting at least one peptide spanning at least one epitope on HPV-16 E7 and E6 polypeptides, said peptide having a sequence selected from the group consisting of
      HPV-16 E7 aa6–35 characterized by the amino acid sequence
         PTLHEYMLDLQPETTDLYCYEQLNDSSEEE (SEQ ID NO: 1),
      HPV-16 E7 aa29–52 characterized by the amino acid sequence
         NDSSEEEDEIDGPAGQAEPDRAHYN (SEQ ID NO: 2),
      HPV-16 E6 aa1–23 characterized by the amino acid sequence
         MHQKRTAMFQDPQERPRKLPQLC (SEQ ID NO: 3), and
      HPV-16 E6 aa8–37 characterized by the amino acid sequence
         MFQDPQERPRKLPQLCTELQTTIHDIILEC (SEQ ID NO: 4)
   or a peptide derived therefrom, with a serum specimen from an individual; and
   b) detecting the reaction product formed by the contacting step with a labeled second antibody.

2. The method according to claim 1, wherein said peptides are HPV-16 E7-gene derived peptides.

3. The method according to claim 2, wherein said peptide is HPV-16 E7 aa6–35 characterized by the amino acid sequence PTLHEYMLDLQPETTDLYCYEQLNDSSEEE (SEQ ID NO: 1).

4. The method according to claim 2, wherein said peptide is HPV-16 E7 aa29–52 characterized by the amino acid sequence NDSSEEEDEIDGPAGQAEPDRAHYN (SEQ ID NO: 2).

5. The method according to claim 1, wherein said peptides are HPV-16 E6-gene derived peptides.

6. The method according to claim 5, wherein said peptide is HPV-16 E6 aa1–23 characterized by the amino acid sequence MHQKRTAMFQDPQERPRKLPQLC (SEQ ID NO: 3).

7. The method according to claim 5, wherein said peptide is HPV-16 E6 aa8–27 characterized by the amino acid sequence MFQDPQERPKLPQLCTELQTTIHDIILEC (SEQ ID NO: 4).

8. The method according to claim 1, wherein a plurality of said peptides are contacted with a serum specimen from an individual.

* * * * *